United States Patent [19]

Johnson et al.

[11] 4,018,797

[45] Apr. 19, 1977

[54] INTERMEDIATES FOR PROSTAGLANDINS

[75] Inventors: Francis Johnson, Setauket, N.Y.;
Kenneth G. Paul, West Newton, Mass.; Duccio Favara, Como, Italy

[73] Assignee: The Dow Chemical Company, Midland, Mich.

[22] Filed: Feb. 18, 1975

[21] Appl. No.: 550,402

Related U.S. Application Data

[63] Continuation-in-part of Ser. No. 447,103, March 1, 1974, abandoned.

[52] U.S. Cl. .................... 260/343.3 R; 260/345.8;
260/468 D; 260/483; 260/488 R
[51] Int. Cl.[2] ....................................... C07D 307/93
[58] Field of Search ................................ 260/343.3

[56] References Cited

OTHER PUBLICATIONS

House, Modern Synthetic Reactions, pp. 10, 71, 91–96.

*Primary Examiner*—Robert Gerstl
*Attorney, Agent, or Firm*—Theodore Post; C. Kenneth Bjork

[57] ABSTRACT

Intermediates for prostaglandins are synthesized from racemic malic acid and enantiomeric d- and l-malic acid derivatives. The novel synthesis of this invention offers the possibility of a stereoselective control of the reaction products to give optically-active derivatives.

2 Claims, No Drawings

INTERMEDIATES FOR PROSTAGLANDINS

CROSS-REFERENCE TO RELATED APPLICATION

This application is a continuation-in-part of U.S. patent application Ser. No. 447,103, filed Mar. 1, 1974, now abandoned.

BACKGROUND OF THE INVENTION

The prostaglandins are members of a family of hormonal substances which have very potent physiological effects. Among these effects, the abortifacient, antihypertensive and bronchodilating properties are the most widely investigated; but other important biological actions have been evidenced by several authors. See, for instance, the review by M. P. L. Caton in "progress in Medicinal Chemistry" Volume 6, part 2, page 317, edited by G. Ellis and G. B. West, Butterworth & Co., London 1971. The prostaglandins are optically active derivatives of prostanoic acid, i.e., a substituted cyclopentane compound having the following structure:

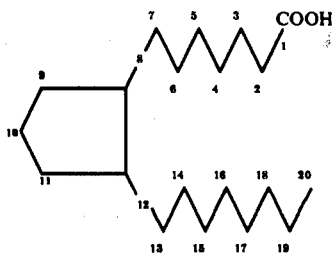

Although they are naturally occurring in a number of tissues, many chemical approaches to their synthesis have been reported in the literature as their concentration in said tissues is very low.

One of the most convenient approaches to the total chemical synthesis of prostaglandins is reported by E. J. Corey and coworkers, *J. Am. Chem. Soc.*, 91, 5675 (1969). This approach requires the synthesis of suitable precursors which are derivatives of the lactone of 2-hydroxy-1-cyclopentaneacetic acid. The synthetic pathway reported by E. J. Corey and coworkers in J.A.C.S. 92, 397, 1970 for optically-active prostaglandins as the naturally occurring forms, requires resolution of an intermediate (+)-cyclopentenehydroxy acid by means of (+)-ephedrine salts to obtain the (−)-isomer. The latter is then transformed into the lactone, which is the key compound for a synthetic stereo-controlled route to prostaglandins in the F and E series, i.e., those having oxy functions at positions 9 and 11. Prostaglandins E may be further transformed into prostaglandins A according to literature methods.

SUMMARY OF THE INVENTION

This invention concerns a new synthetic route for preparing the lactones of hydroxycyclopentaneacetic acid of the formula

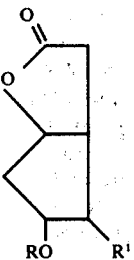

and its optically-active forms

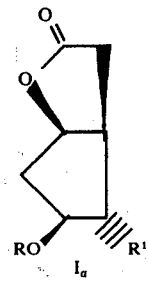 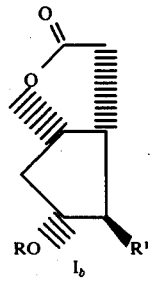

wherein:

R represents hydrogen, lower alkyl of 1 to 6 carbon atoms, e.g., methyl, ethyl, propyl, butyl, pentyl or hexyl; benzyl; trityl; lower alkoxy-lower alkyl, wherein lower alkoxy designates a 1 to 4 carbon atom alkoxy group, e.g., methoxy, ethoxy, propoxy or butoxy and lower alkyl has the meaning previously given; tetrahydropyranyl or an acyl radical selected from alkanoyl of 2 to 8 carbon atoms, e.g., acetyl, propionyl, butyryl, pentanoly, hexanoyl, heptanoyl, octanoyl; benzoyl or substituted benzoyl, wherein the substituents are selected from chloro, bromo, fluoro, lower alkyl (as previously defined), phenyl and cyclohexyl; $R^1$ represents a $CH_2OH$, COOH or $COOR^2$ group wherein $R^2$ is lower alkyl, as previously defined, phenyl or benzyl. In the formulas given above and in the specification and claims, the bonds which have the α-configuration extend behind the plane of the paper and are represented by broken lines, while the bonds which have the β-configuration extend out of the plane of the paper and are represented by thickened lines.

The synthetic route of this invention does not require resolution of racemic mixtures when optically-active end compounds are desired, but allows the use of optically active starting materials whose chiral center surprisingly controls the stereochemistry of all the subsequent reaction steps to afford a predetermined compound of the preceding series Ia or Ib. The process of this invention is a multistep synthesis involving a large number of typical chemical reactions, all of which types are known to those skilled in the art. The process of this invention lies in the application of these known typical chemical reactions to the proper starting materials under proper conditions to arrive at the desired products.

DESCRIPTION OF THE PREFERRED EMBODIMENTS

The starting material for this synthesis is an anhydride of a malic acid derivative wherein the hydroxy group has been protected by acylation. The series of reactions involved in this synthesis may be depicted by the following schematic representation which refers to the synthesis of an optically-active end compound and therefore requires the use of optically-active starting materials such as an l-malic acid anhydride derivative represented by following formula II. The use of a racemic or d-malic acid anhydride derivative according to the same reaction scheme and under the same conditions leads, respectively, to an optically inactive end compound or to the enantiomeric mirror image forms.

STEP A

In the starting compound II, the symbol A represents an acyl radical, as previously defined, or a (di-lower alkyl)carbamyl or a (lower alkoxy)carbonyl radical, lower alkyl and lower alkoxy the same as defined above. The preparation of these compounds may be carried out substantially according to the method described in the literature for preparing the anhydride of the l-isomer of O-acetylmalic acid; Beilstein, 4th Ed., Vol. 18, page 81 and B. Jones, J. Chem Soc. 136, 1933, page 788.

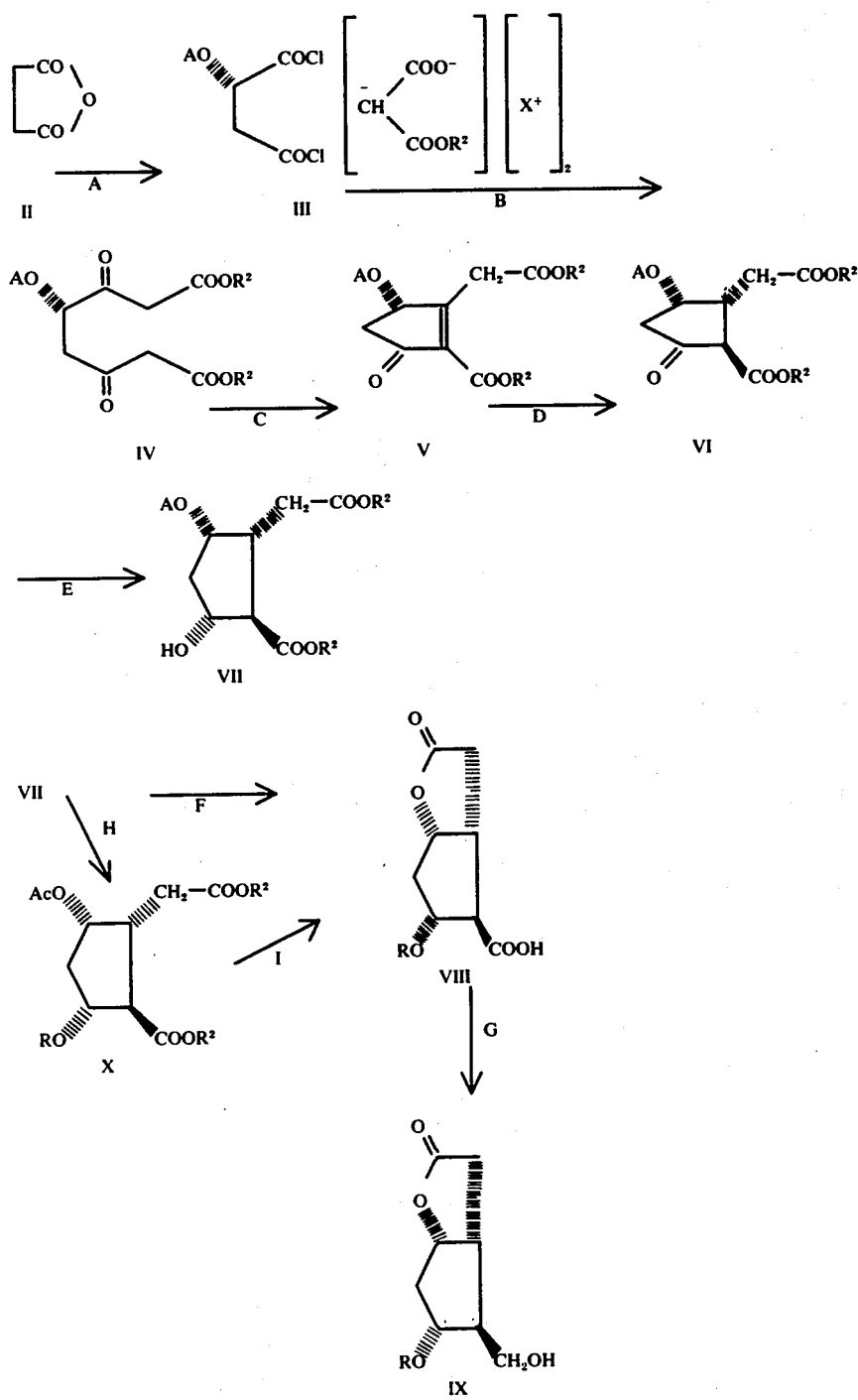

The preferred acylating agents for use in the process are acetic acid anhydride, acetyl chloride and benzoyl chloride. The conversion of the anhydride to the acid chloride III is effected by adding to the protected anhydride of l-malic acid an excess of 1,1-dichloromethyl methyl ether and anhydrous $ZnCl_2$ and refluxing the mixture for about 2 to 6 hours. The resulting compound III may be purified by distillation.

STEP B

One molar proportion of the protected l-malic acid chloride III is treated with about five molar proportions of a hydrogen malonate salt of the formula indicated about wherein $X^+$ represents an alkali metal cation or a monovalent magnesium cation selected from the group $MgBr^+$, $MgCl^+$ and $MgI^+$, and $R^2$ represents lower alkyl, as defined, phenyl or benzyl. The temperature of the reaction may vary from $-30°$ to $+30°$ C. and the reaction time between 5 and 24 hours. The solvent is advantageously selected from one of the anhydrous inert organic solvents such as the lower alkyl ethers, dioxane, and tetrahydrofuran (THF). THF is the preferred solvent. The reaction product IV is recovered by removing the solvent under high vacuum.

STEP C

To obtain the cyclopentenone V from the diketone IV, the intermediate obtained in step B is stirred for 0.5 to 2.5 hours in a buffered solution having a pH value ranging from about 5 to about 11, preferably from 6 to 9. The buffered solution is prepared, for example, by adding triethanolamine to aqueous HCl; or an alkali metal or alkaline earth metal carbonate, bicarbonate citrate or phosphate may also be utilized for this purpose. Advantageously, a calcium or magnesium carbonate which also encompasses a commercial grade, e.g., an oxide-carbonate such as commercial $MgCO_3$ containing 40 percent MgO, may be utilized. An excess wherein undissolved $MgCO_3$ is present is preferred. The cyclization of diketones derived from l-malic acid leads to cyclopentenones having the substituent AO with an α-configuration. The use of d-malic acid derivatives affords products with the β-configuration.

STEP D

Hydrogenation of the double bond of the cyclopentenone V involves stereochemical problems, as the resulting cyclopentanone VI must have the two substituents which are precursors of the side chains of prostaglandins in the desired configuration. For instance, the optically active intermediates I which are useful for the synthesis of naturally occurring prostaglandins must have the substituent $R^1$ in the β-configuration and the methyl-carbonyl group which originates the lactone ring in the α-configuration.

One of the main features of the process of this invention lies in the fact that the original configuration of the group AO determines the configuration of the products of hydrogenation. In fact, when said group has the α-configuration, the resulting products assume the correct configuration with respect to the two adjacent chiral centers, so that the subsequent steps may lead to the desired lactone Ib. When the AO group has the β-configuration, the resulting intermediates have the opposite configuration, leading to lactones of the series I which allow the synthesis of mirror-image forms of naturally-occurring prostaglandins. A reducing agent which is advantageously employed in step D is hydrogen gas in the presence of a noble metal or a noble metal oxide as the hydrogenation catalyst. As an example, Pd supported on barium sulfate or charcoal or $PtO_2$ poisoned with a trace of pyridine gives excellent results. The hydrogenation is carried out in an inert organic solvent, preferably an aromatic solvent such as, for example, benzene, at a pressure ranging from atmospheric to 5 atmospheres pressure.

STEP E

This step involves the reduction of the keto group positioned on the cyclopentane ring of compound VI to a hydroxy group. This function in the precursors for the synthesis of naturally-occurring prostaglandins must have the α-configuration.

A further surprising result of the process is that the reduction of compound VI leads to a derivative having the required configuration. Of course, the stereochemistry is completely opposite if, as a starting material, a cyclopentanone compound is employed derived from an intermediate V having the group AO- in the β-configuration.

It has been found in accordance with this invention that the use of sodium borohydride in the buffer solution at a pH value ranging from 3 to 9, and preferably from 4 to 7.5 is particularly well suited for the stereoselective reduction of the keto group. The buffer solution may be suitably prepared by using an alkali metal phosphate, citrate or monophthalate. The operations of steps D and E may be combined in a single step, although without any substantial improvement of yield, by reducing directly compound V with an alkali metal borohydride or by catalytic hydrogenation in a lower alkanol, preferably at a higher pressure range (5–30 atmospheres) to speed up the rate of reduction of the keto group.

STEP F

Alkaline hydrolysis of compound VII followed by acylation affords the lactone of hydroxycyclopentaneacetic acid, VIII. The alkaline hydrolysis may be carried out according to common procedures. Alkali metal carbonates and alkali metal hydroxides in lower alkanols or in mixtures of water and water-miscible organic solvents are well suited for carrying out this operation but, of course, other analogous conditions and procedures may be used for the ester cleavage.

The temperature of the hydrolysis reaction may vary from about 0° C. to about 30° C. Acylation of the hydroxy group with simultaneous lactonization may be performed directly on the crude reaction product. Suitable acylating agents are the halides or anhydrides of lower aliphatic carboxylic acids of 2 to 8 carbon atoms, benzoic acid and substituted benzoic acid wherein the substituents are selected from chloro, bromo, fluoro, lower alkyl, phenyl and cyclohexyl.

The lactonization may also be carried out in a lower alkanol saturated with dry hydrogen chloride. In this case, compounds of formulas I, Ia and Ib are obtained wherein R is hydrogen and $R^1$ is a lower carboalkoxy group. These compounds may also be obtained by cleavage of the esters of formula VII with an alkali metal carbonate in an anhydrous lower alkanol medium.

STEP G

The reduction of the carboxylic group in compound VIII requires the use of agents which do not affect the other carbonyl groups in the molecule. For example, diborane is known to be more reactive toward carboxylic groups than toward ester or lactone groups.

A preferred method involves conversion of the acid functionality to a carbonyl halide, to a mixed anhydride or to a reactive amide such as the imidazolide. The conversion to a carbonyl halide is carried out by means of a halogenating agent such as, for example, $SOCl_2$ or 1,1-dichloromethyl methyl ether in the presence of $ZnCl_2$. Mixed anhydrides are generally formed by reaction with a lower alkyl chlorocarbonate. The imidazolide, the acid halide or the anhydride is then reduced with an excess of sodium borohydride.

STEP H

A different pathway is followed for preparing end compounds IX wherein the group RO is an ether group. In this case, the hydroxy compound VII is reacted with an agent capable of forming an ether group to give a compound of formula X wherein R is lower alkyl, benzyl, trityl, lower alkoxy-lower alkyl or tetrahydropyranyl. Reagents which may be employed for this preparation include lower alkyl halides of 1 to 6 carbon atoms, benzyl halides, trityl halides, lower alkanols, dihydropyran and lower alkyl-lower alkenyl ethers such as, for example, ethyl vinyl ether in the presence of an acidic catalyst.

STEP I

Hydrolysis of above compound X under the same hydrolytic conditions as in step F, followed by acidification with a mild acid affords the carboxylic compound VIII wherein RO represents an ether group as defined under step H. The latter is reduced to the corresponding alcohol following the same conditions described under step G.

An alternative procedure for preparing the carboxylic compound VIII wherein RO is an ether group involves hydrolytic cleavage of compound VII according to the conditions outlined under step E, followed by neutralization and reaction with a reagent capable of forming an ether linkage instead of an acylating agent. Reagents which may be employed for this step are essentially those listed under step H. Lower alkyl-lower alkenyl ethers and dihydropyran are particularly well suited for this purpose.

The following additional description and examples further describe the invention and the manner and process of making and using it to enable the art skilled to make and use the same and set forth the best mode contemplated by the inventors of carrying out the invention.

EXAMPLE 1

Preparation of Compound III, 1-Acetoxysuccinoyl Chloride l-Malic acid (25 g., 0.19 mole) is transformed to l-2-acetoxysuccinic anhydride according to literature methods by refluxing it in 30 ml. of acetyl chloride. The solution of the anhydride resulting from the reaction, is cooled and an excess of 1,1-dichloromethyl methyl ether (70 g., 0.57 mole) and anhydrous $ZnCl_2$ (500 mg.) is added. After refluxing for four hours, the solution is cooled. Benzene (500 ml.) is then added thereto and the solution after decantation is filtered and evaporated in vacuo. The residue is l-2-acetoxysuccinoyl chloride which may be purified by distilling at 75°–78° C/0.05 mm. Hg $[\alpha]_d^{25}$: −10° (c=1% in $CHCl_3$). The yield is about 80%. The corresponding d- and racemic compounds are prepared according to the same procedure. The dl- mixture and the optically-active benzoyloxysuccinoyl chlorides are prepared accordingly. Their yields are 80–85%. These chlorides are not distillable without decomposition and, therefore, they are used as such in subsequent reactions. An analytical sample of l-2-benzoyloxysuccinoyl chloride, distilled at 140°–143° C/0.5 mm. Hg, had the following microanalysis.

Analysis for $C_6H_6O_4Cl_2$, percent: Calculated C, 33.83, H, 2.83, Cl, 33.28; Found C, 34.08, H, 2.81, Cl, 33.12.

EXAMPLE 2

Preparation of Compound IV, l-3,6-Dioxo-4-Acetoxyoctanedioic Acid Dimethyl Ester To a vigorously stirred suspension of magnesium (72 g., 3.0 moles) in 1000 ml. of (tetrahydrofuran) (THF) (freshly distilled from lithium aluminum hydride), ethyl bromide (350 g., 3.2 moles) is added at such a rate as to maintain a temperature of 30°–35° C. If, after addition, unreacted magnesium is present, 10 g. of ethyl bromide is added and the reaction is refluxed for one hour. Then the water in the condenser is turned off and a stream of nitrogen is passed over the reaction to remove excess ethyl bromide. The solution is then cooled to −20° C by an ice-acetone bath and 2500 ml. of THF is added. Then maintaining a temperature below −10° C, methyl hydrogen malonate (177 g., 1.5 moles) in 500 ml. of THF is added. After addition is complete, the solution is refluxed for two hours, then cooled to 25° C and l-2-acetoxysuccinoyl chloride (63.6 g., 0.3 moles) is added.

After stirring overnight, the solution is poured into 1800 ml. of 1N hydrochloric acid. The THF layer is then washed with successive 500 ml. volumes of a 1M phosphate buffer (pH 6.5) until the pH of the buffer is unchanged. Drying of the organic layer ($MgSO_4$) and evaporation leaves a crude product (70 g.) which exhibits spectral properties identical to the known material. This unstable titular product is used as soon as possible. The corresponding d-derivative and the racemic mixture of enantiomers are prepared similarly. The dimethyl esters of the racemic and of the optically-active 3,6-dioxo-4-benzoyloxyoctanedioic acids are prepared under conditions essentially identical with those described for the acetoxy derivatives. The products are not purified for subsequent reaction.

EXAMPLE 3

Preparation of Compound V, 5-Acetoxy-2-Carbomethoxy-3-Oxo-1-Cyclopenteneacetic Acid Methyl Ester A solution of 70 g. of the dimethyl ester of l-3,6-dioxo-4-acetoxyoctanedioic acid (IV) in 500 ml. of ether is added to a vigorously stirred suspension of 30 g. of $MgCO_3$ (commercial product containing 40 percent MgO) in 1000 ml. of $H_2O$. Almost immediately the pH of the solution becomes 6.0–6.5 and remains in this range throughout the reaction. After thirty minutes, the reaction is filtered and the ether and aqueous layers separated. The ether layer is washed with 100 ml. of 1M phosphate buffer (pH 7). The combined aqueous layers are acidified with concentrated hydrochloric acid, saturated with sodium chloride and extracted with three 500 ml. volumes of ethyl acetate. Drying (MgSO₄) and evaporation of the ethyl acetate gives 55 g. of oil which quickly crystallizes. Recrystallization from carbon tetrachloride gives the titular product (41 g., 50 percent yield from 1-2-acetoxysuccinoyl chloride) of white crystals identical in every way with known material. Pursuant to the same procedure, the d-acetoxyoctanedioic acid derivative gives a cyclopentene derivative of formula V wherein the acetoxy group has the β-orientation. The dl-acetoxy and benzoyloxy analogs and the enantiomeric d- and l- benzoyloxyoctanedioic acid analogs, are prepared according to the same procedure.

EXAMPLE 4

Preparation of Compound VI, 2-Carbomethoxy-3-Oxo-5-Acetoxycyclopentaneacetic Acid Methyl Ester The cyclopentene acid, V, (9.5 g.) is dissolved in 180 ml. of benzene and the solution is hydrogenated at room temperature and atmospheric pressure in the presence of 0.5 g. of palladiated barium sulfate. When the theoretical amount of hydrogen is absorbed, catalyst is filtered off and the solution is evaporated to dryness under vacuum, yielding 9 g. (95%) of the methy ester of 2-carbomethoxy-3-oxo-5-acetoxycyclopentaneacetic acid with the required stereochemical configuration. The compound is a rather unstable solid, melting at 54° C; $[\alpha]_d^{25}$:−17.8 (C=1.017% in CHCl₃).

Analysis for $C_{12}H_{16}O_7$, percent: Calculated C, 52.94, H, 5.72; Found C, 53.14 H, 5.91.

I.R., N.M.R. and mass spectral data are in agreement with the assigned structure. The use of different catalysts such as Pd, PtO₂ and Rh has little effect on the final yields. The same reaction conditions are suitable for preparing the racemate, the mirror image isomer and all the corresponding 5-benzoyloxy derivatives.

EXAMPLE 5

Preparation of Compound VII, 5-Acetoxy-2-Carbomethoxy-3-Hydroxycyclopentaneacetic Acid Methyl Ester The cyclopentanone VI (8.6 g.), obtained according to the previous example, is dissolved in 50 ml. of methanol and added to 500 ml. of a phosphate buffer adjusted to a pH of 5.3. Then 20 ml. of an aqueous solution containing an excess of sodium borohydride (1.25 g.) is added at 5° C. After two hours at room temperature, 200 ml. of water is added to the reaction mixture which is then extracted several times with ethyl acetate. The combined organic layers are dried on MgSO₄ and then evaporated to dryness giving 8.4 g. (98%) of crude methylester of 5-acetoxy-2-carbomethoxy-3-hydroxycyclopentaneacetic acid. This product examined by gas chromatography exhibits an 80% purity. The product which may be further purified by column chromatography has all the substituent groups with the desired orientation. The compound may not be distilled without decomposition. The principal absorption peaks in the N.M.R. spectrum in CDCl₃ occur at the following frequencies expressed in δ units: 2.05 (3H, singlet), 3.65 (3H, singlet), 3.72 (3H, singlet), 4.30–4.70 (1H, multiplet, 5.18–5.43 (1H, multiplet).

The I.R. spectrum (neat) shows characteristic bands at the following frequencies:

3450, 2920, 1730, 1725, 1710, 1435, 1370, 1270, 1240, 1200, 1160, 1040, 1020, 950, 890 cm.⁻¹

Analysis calculated for $C_{12}H_{18}O_7$, percent: Calculated C, 52.55, H, 6.60; Found C, 52.16, H, 6.59.

The racemic mixture, the mirror image compound and all corresponding benzoyloxy derivatives are prepared by following essentially the same procedure.

The methyl ester of 5-acetoxy-2-carbomethoxy-3-hydroxy-cyclopentaneacetic acid may be prepared in a 60% yield by reducing directly the methyl ester of 5-acetoxy-2-carbomethoxy-3 -oxo-1-cyclopenteneacetic acid, VI, with sodium borohydride. The reaction conditions are essentially identical with those described above.

An alternative direct method involves stirring for 5 hours in an autoclave under 15 atmospheres of hydrogen the methyl ester of 5-acetoxy-2-carbomethoxy-3-oxo-1-cyclopenteneacetic acid (200 mg.) dissolved in 15 ml. of methanol in the presence of 20 mg. of PtO₂. Removal of the catalyst and of the solvent gives 200 mg. of a crude oil which contains about 60% of the desired isomer (determined by gas chromatography).

EXAMPLE 6

Preparation of Compound VIII, Lactone of 3-Acetoxy-2-Carboxy-5-Hydroxycyclopentaneacetic Acid The methyl ester of 5-acetoxy-2-carbomethoxy-3-hydroxy-cyclopentaneacetic acid (95 mg.) in one milliliter of methanol is added at 0° C under a nitrogen atmosphere to a solution of 180 mg. of potassium hydroxide in 3 ml. of methanol. After standing at room temperature for four hours, 1.2 g. of Amberlite CG 120 is added and the mixture is stirred for two minutes. After filtration of the solid the methanol is evaporated off. To the residue, 1 ml. of acetyl chloride is added and the mixture is allowed to stand at room temperature for three hours. The acetyl chloride excess is evaporated off at 30° C and the residue is taken up with water, from which the lactone of 3-acetoxy-2-carboxy-5-hydroxycyclopentaneacetic acid crystallizes out. Yield 54 mg. (67%).

The product when crystallized from water melts at 205°–206° C$[\alpha]_d^{25}$:−90.1 (c=1.1% in pyridine).

Analysis calculated for $C_{10}H_{12}O_6$, percent: Calculated C, 52.63, H, 5.30; Found C, 52.80, H, 5.40.

The N.M.R., I.R. and mass spectral data are in accordance with the lactonic structure, VIII, (R=CH₃CO), i.e., a compound of the formula Ib wherein R is acetyl and R¹ is COOH. The same lactone VIII is obtained by employing as the starting material the methyl ester of 5-benzoyloxy-2-carbomethoxy-3-hydroxycyclopentaneacetic acid. The above described conditions are suitable also for preparing the corresponding racemate and the mirror image enantiomers falling respectively within the scope of formulas I and Ia, by utilizing the proper starting materials.

The acid cleavage of the methyl ester, VII, is carried out by dissolving the compound (5 g.) in 20 ml. of methanol and adding the solution to 70 ml. of methanol saturated with dry hydrogen chloride. The reaction mixture is maintained at 0° C for eight hours, then the solvent is evaporated off. The residue is purified by crystallization from ethyl ether. The product obtained in a 45 percent yield is the lactone of 2-carbomethoxy-3,5-dihydroxycyclopentaneacetic acid, i.e., compound Ib wherein R is hydrogen and R¹ is carbomethoxy.

The product melts at 103° C; $[\alpha]_d^{25}$:—15.9° (c=1.95L % in $CHCl_3$) Analysis calculated for $C_9H_{12}O_5$, percent: Calculated C, 53.99 H, 6.04; Found C, 54.26 H, 6.16.

The I.R., N.M.R. and mass spectrometry data confirm the assigned structure. The above lactone is also obtained, in a 70% yield, by cleavage of the ester VII with $K_2CO_3$ in anhydrous methanol at room temperature.

EXAMPLE 7

Preparation of Compound IX, γ-Lactone of 3-Acetoxy-2-Hydroxymethyl-5-Hydroxycyclopentaneacetic Acid The lactone of 3-acetoxy-2-carboxy-5-hydroxycyclopentaneacetic acid, VIII (410 mg.), obtained pursuant to Example 6 is dissolved in 10 ml. of dichloromethane under a nitrogen atmosphere and to the so-obtained solution cooled to −10° C, 200 mg. of triethylamine is added followed by 216 mg. of ethyl chlorocarbonate in 5 ml. of dichloromethane. After stirring for one hour at a temperature between −15° C and −10° C, the solution is added to 150 mg. of sodium borohydride in 30 ml. of dry ethanol at −30° C. The mixture is stirred at a temperature between −30° C and −10° C for one hour, then is poured into 30 ml. of water containing 0.005 mole of monosodium citrate. The aqueous solution is extracted with ethyl acetate and the organic layer, after washing with aqueous sodium bicarbonate and water, is dried over $MgSO_4$ and evaporated to give 376 mg. (98%) of an oily product which is the lactone of formula IX wherein R is acetyl. Specific rotation, I.R. and N.M.R. data confirm that this product is identical with the intermediate described by Corey et al., J.A.C.S. 92, 397 (1970). The same product may be prepared by reducing with sodium borohydride the chloride of the acid of formula VIII. The acid is converted to the corresponding chloride by heating at 60° C for 5 minutes with $SOCl_2$ in the presence of traces of dimethylformamide or by reaction with 1,1-dichloromethyl methyl ether and $ZnCl_2$. Evaporation of the volatile materials affords a crude product which is directly reacted with $NaBH_4$ in dry ethanol. The yield is of about 95%.

The corresponding racemate and mirror image compound are prepared by pursuing essentially the same procedures.

EXAMPLE 8

Preparation of Compound X, 5-Acetoxy-2-Carbomethoxy-3-Tetrahydropyranyloxycyclopentaneacetic Acid Methyl Ester The methyl ester of 5-acetoxy-2-carbomethoxy-3-hydroxycyclopentaneacetic acid of formula VII (5.8 g.) is dissolved in 50 ml. of anhydrous benzene and to the obtained solution 70 mg. of p-toluenesulfonic acid in 30 ml. of anhydrous benzene are added followed by 1.87 g. of 2,3-dihydropyran. After standing for one hour at the room temperature the solution is poured into aqueous sodium bicarbonate. After extraction with dichloromethane the organic solution is dried over $Na_2SO_4$ and evaporated to give 6.9 g. (90%) of an oily product which is the methyl ester of 5-acetoxy-2-carbomethoxy--3-tetrahydropyranyloxycyclopentaneacetic acid. the principal absorption peaks in the N.M.R. spectrum in $CDCl_3$ occur at the following frequencies expressed in δ units:

1.6 (6H, multiplet), 2.02 (3H, singlet), 3.65 (3H, singlet), 3.7 (3H, singlet), 4.3–4.8 (2H, multiplet) 5–5.35 (1H, multiplet)

The I.R. spectrum (neat) shows characteristic bands at the following frequencies:

2930, 1740, 1440, 1380, 1240, 1200, 1170, 1135, 1080, 1030, 970, 870, 820 cm.$^{-1}$

Analysis calculated for $C_{17}H_{26}O_8$, percent: Calculated C, 56.97, H, 7.31; Found C, 56.65, H, 7.43.

The assigned structure is supported also by U.V. and mass spectral data. The racemate, the mirror image enantiomer and the benzoyloxy derivatives are prepared pursuant to the same methods.

EXAMPLE 9

Transformation of Compound X to Compound IX

The methyl ester of 5-acetoxy-2-carbomethoxy-3-tetrahydropyranyloxycyclopentaneacetic acid (0.95 g.) in 15 ml. of dioxane is added under a nitrogen atmosphere to a solution of 0.75 g, of KOH in 15 ml. of water. After standing at room temperature overnight, the mixture is washed with ethyl ether and the aqueous phase is acidified with 5 g. of citric acid in 50 ml. of ice water. After four extractions with ethyl acetate, the combined organic extracts are dried and evaporated to dryness, giving 0.7 g. (69%) of the lactone of formula VIII wherein R is 2-tetrahydropyranyl, i.e., compound Ib wherein R is 2-tetrahydropyranyl and $R^1$ is COOH; m.p. 156° C.

The compound VIII is then converted in a 95% yield to the corresponding compound of formula IX wherein R is 2-tetrahydropyranyl by following essentially the same procedure described in Example 7. The N.M.R. and I.R. spectral data of the product obtained are in agreement with the assigned structure.

Analysis calculated for $C_{13}H_{20}O_5$, percent: Calculated C, 60.92, H, 7.87; Found C, 60.75, H, 7.77.

Cleavage of the ester, X, with sodium methoxide or potassium carbonate in anhydrous methanol affords a lactone of formula Ib wherein R is tetrahydropyranyl and $R^1$ is $COOCH_3$ in a 70% yield.

EXAMPLE 10

Transformation of Compound VII to VIII

Five hundred milligrams of the methyl ester of 5-acetoxy--2-carbomethoxy-3-hydroxycyclopentaneacetic acid (VII) are hydrolyzed to the lactone of 2-carboxy-3,5-dihydroxycyclopentaneacetic acid by following the same conditions described in the first part of Example 6. After addition of 7 g. of Amberlite CG 120, the residue is crystallized from ethyl acetate, giving 243 mg. (71%) of the pure product (VIII, R=H) which melts at 152° C;$[\alpha]_d^{25}$:—53 (c=0.85% in pyridine). The compound obtained is then reacted with 100 mg. of 2,3-dihydropyran in the presence of p-toluenesulfonic acid (15 mg.) pursuant to the procedure described in Example 8, to give 288 mg. (83%) of the lactone VIII, wherein R is 2-tetrahydropyranyl.

That which is claimed is:

1. A process for preparing a compound of the group having the formula

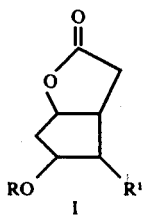

and its optically active forms

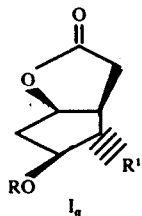 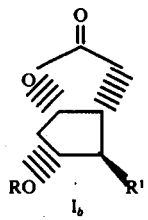

wherein:
R represents acetyl and $R^1$ represents a $CH_2OH$ group, which comprises (1) reacting at about −30° to about +30° C substantially one molar proportion of l-2-acetoxysuccinoyl chloride with substantially five molar proportions of a salt of the formulas

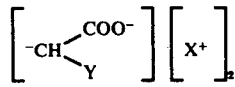

wherein Y represents a $COOR^2$ group wherein $R^2$ is lower alkyl and X is an alkali metal cation selected from $MgBr^+$, $MgCl^+$ and $MgI^+$ whereby a 3,6-dioxo-4-acetoxyoctanedioic acid ester is formed, (2) cyclizing the last named by heating it in an aqueous solution at a pH of about 5 to 11 to give a 5-acetoxy-2-carbo-(lower alkoxy)-3-oxo-1-cyclopenteneacetic acid ester, (3) (a) hydrogenating the cyclopentene ring to cyclopentane with hydrogen in the presence of a noble metal or a noble metal oxide hydrogenation catalyst, (3) (b) reducing the keto group to a hydroxy group with sodium borohydride in an aqueous solution buffered to a pH of about 3 to about 9 to give the methyl ester of 3-acetoxy-2-carbomethoxy-3-hydroxycyclopentaneacetic acid, (4) cyclizing the so-obtained acyloxycyclopentaneacetic acid derivative by alkaline hydrolysis and acylating the hydroxy group with acetyl chloride to the corresponding lactone of preceding formula I, Ia or Ib wherein $R^1$ is a carboxy group and R is acetyl, (5) converting the carboxylic group to a mixed anhydride group by reaction with a lower alkyl chlorocarbonate or to an acid chloride group by reaction with $SOCl_2$ and (6) reducing the mixed anhydride group or the acid chloride group with excess sodium borohydride to give the gamma lactone of 3-acetoxy-2-hydroxymethyl-5-hydroxycyclopentane-acetic acid.

2. The process of claim 1 wherein the acyloxysuccinoyl chloride of step (1) is l-2-acetoxysuccinoyl chloride and the salt is

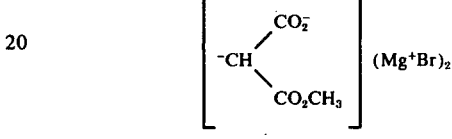

whereby l-3,6-dioxo-4-acetoxyoctanedioic acid dimethyl ester is formed, (2) cyclizing the last named compound by heating it in aqueous solution at a pH of about 6 to 9 to give 5-acetoxy-2-carbomethoxy-3-oxo-1-cyclopenteneacetic acid methyl ester, (3) hydrogenating the cyclopentene ring to cyclopentane with hydrogen in the presence of a noble metal or a noble metal oxide hydrogenation catalyst, (4) hydrogenating the keto group to a hydroxy group with sodium borohydride in an aqueous solution buffered to a pH of about 3 to about 9 to give the methyl ester of 3-acetoxy-2-carbomethoxy-3-hydroxycyclopentaneacetic acid, (5) cyclizing the last named compound via alkaline hydrolysis and acylating the hydroxy group with acetyl chloride to give the lactone of 3-acetoxy-2-carboxy-5-hydroxycyclopentaneacetic acid, (6) converting the carboxy group to a mixed anhydride group by reaction with excess ethyl chloroformate or to an acid chloride group by reaction with $SOCl_2$ and reducing the mixed anhydride group or the acid chloride group with excess sodium borohydride to give the gamma lactone of 3-acetoxy-2-hydroxymethyl-5-hydroxycyclopentaneacetic acid.

* * * * *

UNITED STATES PATENT AND TRADEMARK OFFICE
CERTIFICATE OF CORRECTION

PATENT NO. : 4,018,797
DATED     : April 19, 1977
INVENTOR(S) : Francis Johnson et al.

It is certified that error appears in the above-identified patent and that said Letters Patent are hereby corrected as shown below:

Title page, right hand side, third line, "pp. 10,71, 91-96" should read -- pp. 71, 91-96 --.

Column 1, line 19, "'progress" should read -- "Progress --.

Column 2, line 37, "pentanoly" should read -- pentanoyl --.

Column 3, reaction A of compound II,

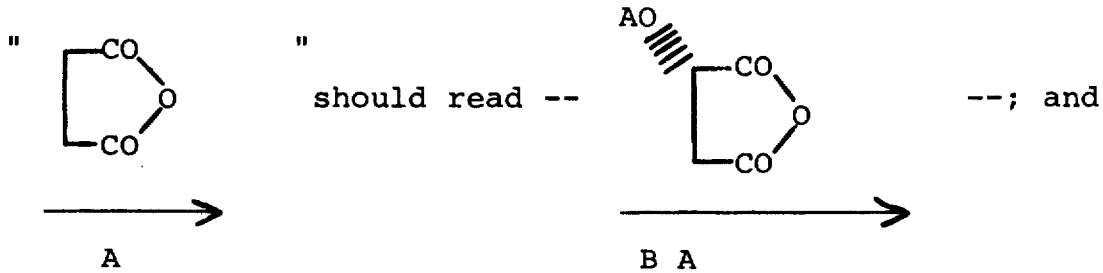

; and

UNITED STATES PATENT AND TRADEMARK OFFICE
CERTIFICATE OF CORRECTION

PATENT NO. : 4,018,797
DATED : April 19, 1977
INVENTOR(S) : Francis Johnson et al.

It is certified that error appears in the above—identified patent and that said Letters Patent are hereby corrected as shown below:

Column 5, line 14, "about" should read -- above --.

Column 9, line 25, "absorbed" should read -- adsorbed --; and
        line 28, "methy" should read -- methyl --.

Column 11, line 1, "(c=1.95L" should read -- (c=1.95 --.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks